(12) United States Patent
Kaufman et al.

(10) Patent No.: US 6,190,606 B1
(45) Date of Patent: Feb. 20, 2001

(54) SOLID AMALGAMATING COMPOSITIONS FOR THE PREPARATION OF DENTAL AMALGAMS, AMALGAM FORMING COMPOSITIONS CONTAINING THEM, METHODS FOR PRODUCING DENTAL AMALGAMS WITH THEM AND DENTAL AMALGAMS PRODUCED THEREBY

(75) Inventors: Alberto Kaufman; Baruch Kopeliovich, both of Haifa; Moshe Zalsman, Ramot Hashavim, all of (IL)

(73) Assignee: Silmet Ltd., Or Yehuda (IL)

( * ) Notice: Under 35 U.S.C. 154(b), the term of this patent shall be extended for 0 days.

(21) Appl. No.: 09/133,688

(22) Filed: Aug. 13, 1998

(30) Foreign Application Priority Data

Aug. 19, 1997 (IL) ......................................... 121581
Feb. 19, 1998 (IL) ......................................... 123376

(51) Int. Cl.[7] ...................................... C22C 7/00
(52) U.S. Cl. .......................................... 420/527; 420/526
(58) Field of Search ....................................... 420/527, 526

(56) References Cited

U.S. PATENT DOCUMENTS 3,839,780 * 10/1974 Freedman et al. .
4,264,354 * 4/1981 Cheetham .
4,686,082 * 8/1987 Parker ................................... 420/503
5,185,125 * 2/1993 Smith et al. .......................... 420/503
5,516,355 * 5/1996 Rahdakrishnan ....................... 75/351

OTHER PUBLICATIONS

Foreign Patent Document, PCT/IL96/00167 (Publication No. WO 97/26384), Isreal, Jul. 24, 1997.

* cited by examiner

Primary Examiner—John Sheehan
(74) Attorney, Agent, or Firm—Miles & Stockbridge; Dennis P. Clarke

(57) ABSTRACT

The present invention concerns totally solid amalgamating compositions particularly useful in the preparation of dental amalgams for filling cavities and similar dental applications, comprising one or more solid amalgamating alloys, metals and/or intermetallic compounds or combinations thereof, amalgam forming compositions containing such totally solid amalgamating compositions, methods for producing dental amalgams with such totally solid amalgamating compositions or amalgam forming compositions containing them, and denial amalgams produced thereby.

78 Claims, No Drawings

SOLID AMALGAMATING COMPOSITIONS FOR THE PREPARATION OF DENTAL AMALGAMS, AMALGAM FORMING COMPOSITIONS CONTAINING THEM, METHODS FOR PRODUCING DENTAL AMALGAMS WITH THEM AND DENTAL AMALGAMS PRODUCED THEREBY

FIELD OF THE INVENTION

The present invention relates to the field of dentistry and to improved amalgamating methods and amalgam forming compositions for the preparation of dental amalgams used to fill dental cavities.

BACKGROUND OF THE INVENTION

To facilitate a better understanding for the background of the present invention and the invention itself, the following definitions are hereby provided:

Amalgamating Composition—One or more amalgamating alloys, metals and/or intermetallic compounds or combinations thereof, that upon trituration with an Amalgamable Composition (see below), produce an amalgam (see below).

Amalgamable Composition—One or more amalgamable alloys, metals and/or intermetallic compounds or combinations thereof, that upon trituration with an Amalgamating Composition (see above), produce an amalgam (see below).

Amalgam Forming Composition—A composition that forms an amalgam upon trituration. Such compositions comprise an Amalgamating Composition (see above), until now for the most part, usually liquid mercury, and an Amalgamable Composition (see above). Such amalgams are in wide use in the field of dentistry.

The usual material used for filling dental cavities is based on amalgam obtained when suitable alloys, usually silver based, are triturated with inercury. The alloys so used are referred to herein as amalgamable materials. While the mercury so used, is referred to as an amalgamating material, other amalgamating materials, for the most part based on liquid combinations of indium and mercury, have also been described.

In an earlier patent application, now published as PCT/IL96/00167, there is described improved compositions for the formation of dental amalgams. The improvements in the said compositions were based on the development and utilization of improved amalgamable alloys and combinations of metals, as well as the use of liquid indium-mercury combinations mentioned above.

The information and disclosures of PCT/IL96/00167 are included herein by reference.

The usual liquid mercury and liquid mercury based amalgamating alloys are clumsy to handle, likely to spill and are not easy to recover, should a spill occur.

SUMMARY DESCRIPTION

The present invention provides new, totally solid, amalgamating compositions. The invention also provides new, totally solid, amalgam forming compositions. The amalgamating compositions and the amalgam forming compositions of the present invention, as well as their component compositions, may also comprise additional components, that can enhance the properties of the amalgams produced by them or facilitate the amalgam forming reaction.

The solid amalgam producing and amalgamating alloys and combinations so provided, as well as the solid dental amalgams forming compositions comprising them, are easy to handle, less likely to spill and are easy to recover, should a spill occur. In addition, the amalgam producing compositions when triturated per se and the amalgamating alloys and combinations when triturated with suitable amalgamable materials, form conveniently workable plastic amalgams, that upon application to dental cavities set in due course to stable, durable and effective dental fillings.

The solid amalgamating compositions of the present invention are readily converted to dental amalgams, by simple trituration with amalgamable materials.

The solid amalgam forming compositions of the present invention are readily converted to dental amalgams, by simple trituration.

It is an object of certain aspects of the present invention to provide solid amalgamating compositions that form denial amalgams upon trituration with suitable amalgamable compositions.

Consequently, it is also an object of certain aspects of the present invention to provide solid dental amalgam forming compositions, that form workable dental amalgam upon trituration.

It is yet a further object of certain aspects of the present invention to provide improved solid amalgam forming compositions and amalgamating compositions that are easy to handle and relatively easy to recover if inadvertently spilled.

It is yet a further object of certain aspects of the present invention to provide solid amalgamating compositions that upon trituration with amalgamable compositions provide conveniently workable plastic dental amalgam.

It is yet a further object of certain aspects of the present invention to provide solid amalgamating compositions that upon trituration with amalgamable compositions and insertion in dental cavities, harden within a relatively short time to produce chemically and mechanically stable fillings with acceptable or improved effective performance lifetime.

It is yet a further object of certain aspects of the present invention to provide solid dental amalgam forming compositions that upon trituration provide conveniently workable plastic dental amalgam.

It is yet a further object of certain aspects of the present invention to provide solid dental amalgam forming compositions that after trituration and insertion in dental cavities, harden within relatively short time to produce chemically and mechanically stable fillings with an acceptable or improved effective performance lifetime.

It is yet a further object of certain aspects of the present invention to provide methods for producing dental amalgam based on solid amalgamating compositions or solid amalgam forming compositions that after trituration and insertion in dental cavities, harden within relatively short time to produce chemically and mechanically stable fillings with an acceptable or improved effective performance lifetime.

It is yet a further object of certain aspects of the present invention to provide dental amalgams based on solid amalgamating compositions or solid amalgam forming compositions that after trituration and insertion in dental cavities, harden within a relatively short time to produce chemically and mechanically stable fillings with an acceptable or improved effective performance lifetime.

In accordance with one aspect of the present invention, there is provided improved solid amalgamating compositions containing one or more solid amalgamating alloys, metals, and/or intermetallic combinations or combinations thereof, that upon trituration with suitable amalgamable materials produce dental amalgams and chemically and mechanically stable dental cavity fillings with acceptable or improved effective performance lifetime.

In accordance with another aspect of the present invention, there is provided a solid composition for the formation of a dental amalgam comprising;

(a) one or more solid amalgamable alloys, metals and/or intermetallic compounds or combinations thereof, and (b) one or more solid amalgamating alloys, metals and/or intermetallic compounds or combinations thereof, wherein the formation of the dental amalgam is effected by trituration of the solid composition.

In accordance with a further aspect of the present invention, there are provided methods for conveniently producing dental amalgams based on solid amalgamating compositions or solid amalgam forming compositions that after trituration of the amalgamating compositions with amalgamable compositions or trituration of the amalgam forming compositions per se and insertion in dental cavities, the dental amalgams so produced harden within a relatively short time to produce chemically and mechanically stable fillings with an acceptable or improved effective performance lifetime.

In accordance with a further aspect of the present invention, there is provided dental amalgams produced from solid amalgamating compositions or solid amalgam forming compositions that after trituration of the amalgamating compositions with amalgamable compositions or trituration of the amalgam forming compositions per se and insertion in dental cavities, the dental amalgams so produced harden within relatively short time to produce chemically and mechanically stable fillings with an acceptable or improved effective performance lifetime.

DETAILED DESCRIPTION OF THE INVENTION AND EXAMPLES

The present invention provides improved solid amalgamating compositions that upon trituration with suitable amalgamable compositions become a dental amalgam that can be used for filling dental cavities.

The present invention also provides a new totally solid composition that upon trituration becomes a dental amalgam useful for filling dental cavities.

The present invention further provides methods for conveniently producing dental amalgams by trituration of totally solid amalgamating compositions with amalgamable compositions or totally solid amalgam forming compositions that upon trituration becomes a dental amalgam useful for filling dental cavities.

The present invention further provides dental amalgams by trituration of totally solid amalgamating compositions with amalgamable compositions or totally solid amalgam forming compositions.

Normally, dental amalgam is formed by the trituration of an amalgamable alloy or mixture of alloys and/or metals with mercury, or a liquid mercury containing alloy or alloys. Such amalgams usually contain approximately 41% to 54% mercury. Commonly, a multi-component capsule is used for the storage of the amalgamable component with the amalgamating component, initially being separated in the capsule, and subsequently the trituration-mixing being effected therein. Once such a capsule is placed in a trituration machine and the amalgamable component is mixed with the amalgamating component, the ensuing amalgamation reaction effects a hardening of the mixture within a matter of a few minutes, during which, additional shaping, such as by carving, can be carried out for a period of up to about 15 minutes. The amalgamation reaction is usually complete within about 24 hours.

The new, solid amalgamating compositions of the present invention can be stored as a single composition that can be handled and maintained as such until needed, then combined with amaigamable compositions as desired and triturated to form dental amalgam.

The new, amalgam forming compositions of the present invention, can be stored as a single composition that can be handled and maintained as such until needed and is then triturated to form amalgam. The solid form can be for example in powdered or pelletized form. The solid powders and pellets can be provided in commonly known or available, ready to use, dosage and packaging forms, that readily produce dental amalgams. That is to say, upon trituration they provide a plastic, workable dental amalgam, the said plastic dental amalgam hardening in due course, to provide dental cavity fillings of satisfactory chemical and mechanical stability.

The invention can be illustrated by the following examples.

EXAMPLES

Example 1

A powdered mixture composition was prepared with the following components:

(1) Powdered $Mn_2Hg_5$ (20% by wt.), (2) Powdered 68% Ag-25% Cu-7% Pd (50% by wt.) and (3) Powdered 79% In-21% Hg (30% by wt.).

The composition was triturated for 5–6 seconds. The compression strength measured after 1 hour was 299–316 MPa. The compression strength measured after 24 hours was 400–500 MPa.

Example 2

A powdered mixture composition was prepared with the following components:

(1) Powdered $Mn_2Hg_5$ (30% by wt.), (2) Powdered 68% Ag-25% Cu-7% Pd (50% by wt.) and (3) Powdered In (20% by % wt.).

The composition was triturated for 5–6 seconds. The compression strength measured after 1 hour was 310–360 MPa. The compression strength measured after 24 hours was 400–450 Mpa.

Example 3

A powdered mixture composition was prepared with the following components:

(1) Powdered $Mn_2Hg_5$ (23.5% by wt.), (2) Powdered 68% Ag-25% Cu-7% Pd (46.4% by wt.) and (3) Powdered 92% In-8% Hg (30.1% by wt.).

The composition was triturated for 5–6 seconds. The compression strength measured after 1 hour was 300–340 MPa. The compression strength measured after 24 hours was 500–530 Mpa.

Example 4

A powdered mixture composition was prepared with the following components:

(1) Powdered $PdHg_4$ (67.5% by wt.).

(2) Commercial 60% Ag spherical alloy (27% by wt.) and (3) Powdered 96.5% Sn-3.5% Ag(5.5% by wt.).

The composition was triturated for 11–13 seconds. The compression strength measured after 1 hour was 80–100 MPa. The compression strength measured after 24 hours was 300–330 Mpa.

Example 5

A powdered mixture composition was prepared with the following components:
(1) Powdered $PdHg_4$ (53% by wt.),
(2) Commercial 60% Ag spherical alloy (35.5% by wt.)
(3) Powdered 100% Sn (6.5% by wt.)
(4) Powdered $Ag_2Hg_3$ (3.5% by wt.) and
(5) Powdered $ZnHg_3$ (1.5% by wt.).

The coinposition was triturated for 11–13 seconds. The compression strength measured after 1 hour was 130–170 MPa. The compression strength measured after 24 hours was 380–440 Mpa.

Example 6

A powdered mixture composition was prepared with the following components:
(1) Powdered $PdHg_4$ (48by wt.),
(2) Commercial 60% Ag spherical alloy (32% by wt.),
(3) Powdered 77% Sn-23% Hg (9% by wt.) and
(4) Powdered $Ag_2Hg_3$(11% by wt.).

The composition was triturated for 20–23 seconds. The compression strength measured after 1 hour was 150–1 80 MPa. The compression strength measured after 24 hours was 310–340 Mpa.

While certain embodiments of the present invention have been hereinbefore particularly described, it will be apparent to any one skilled in the art that many modifications and variations may be made, that do not deviate from the main features or spirit of the invention. The invention is accordingly not to be restricted to such embodiments, but rather to its concept, spirit and general scope.

What is claimed is:

1. A solid amalgamating composition comprising one or more solid mercury containing alloys, or intermetallic compounds or combinations thereof, that upon trituration With an amalgamable composition provides a dental amalgam.

2. A solid amalgamating composition as in claim 1, comprising $Mn_2Hg_5$.

3. A solid amalgamation composition as in claim 1, comprising an alloy of indium and mercury, which is a solid at room temperature.

4. A solid amalgamating composition as in claim 1, comprising $Mn_2Hg_5$ and an alloy or alloys of indium and mercury, all which are solid at room temperature.

5. A solid amalgamating composition as in claim 1, additionally comprising free indium metal.

6. A solid amalgamating composition as in claim 1, comprising $PdHg_4$ and an alloy or alloys of palladium and mercury, all of which are solid at room temperature.

7. A solid amalgamating composition as in claim 6, further comprising $Ag_xH_y$, wherein $1/3<x/y<2$.

8. A solid amalgamating composition as in claim 6, further comprising tin metal or alloys of tin.

9. A solid amalgamating composition as in claim 6, further comprising an alloy of indium and mercury, which is a solid at room temperature.

10. A solid amalgamating composition as in claim 8 wherein the tin alloy is a eutectic of tin with indium or silver.

11. A solid amalgamating composition as in claim 8 wherein the tin alloy is a tin mercury alloy solid at room temperature.

12. A solid dental amalgam forming composition comprising;
(a) a solid amalgamating composition, comprising one or more solid mercury containing alloys, or intermetallic compounds or combinations thereof and in addition
(b) a solid amalgamable composition comprising one or more solid amalgamable alloys, metals and/or intermetallic compounds or combinations thereof, wherein the formation of the dental amalgam can be effected by trituration of the said solid amalgam forming composition.

13. A solid amalgam forming composition as in claim 12, wherein the solid amalgamating composition comprises $Mn_2Hg_5$.

14. A solid amalgam forming composition as in claim 12, wherein the solid amalgamating composition comprises an alloy of indium and mercury, which is a solid at room temperature.

15. A solid amalgam forming composition as in claim 12, wherein the solid amalgamating composition, comprises $Mn_2Hg_5$ and an alloy or alloys of indium and mercury, all of which are solid at room temperature.

16. A solid amalgam forming composition as in claim 12, wherein the solid amalgamating composition, additionally comprises free indium metal.

17. A solid amalgam forming composition as in claim 12, wherein the solid amalgamating composition, comprises $PdHg_4$ and an alloy or alloys of palladium and mercury, all of which are solid at room temperature.

18. A solid amalgam forming composition as in claim 17 wherein the solid amalgamating composition, further comprises $Ag_xHg_y$, wherein $1/3<x/y<2$.

19. A solid amalgam forming composition as in claim 17, wherein the solid amalgamating composition, further comprises tin metal or alloys of tin.

20. A solid amalgam forming composition as in claim 17, further comprising an alloy of indium and mercury, which is a solid at room temperature.

21. The solid amalgam forming composition as in claim 19 wherein the tin alloy is a eutectic of tin with indium or silver.

22. A solid amalgam forming composition as in claim 19 wherein the tin alloy is a tin mercury alloy solid at room temperature.

23. A solid dental amalgam forming composition as in claim 12, wherein the solid amalgamable composition is silver based.

24. A solid dental amalgam forming composition as in claim 12, wherein the solid amalgamable composition contains 45%–80% silver, 5%–30% copper, 10–35% tin and 0.1%–5% noble metal selected from the group consisting of gold, platinum, palladium or mixtures thereof, and may be further optionally alloyed with one or more of the following; 0.1%–10% indium, 0.1%–5% mercury, 0.1%–5% zinc or any mixtures thereof.

25. A solid dental amalgam forming composition as in claim 12, wherein the solid amalgamable composition contains copper, in an amount between 20%–40%.

26. A solid dental amalgam forming composition as in claim 12, wherein the solid amalgamable composition contains between 1%–8% of palladium, gold, platinum or any mixture thereof.

27. A solid dental amalgam forming composition as in claim 23, wherein the silver based component of the amalgamable composition is initially heat treated to increase amalgam working time.

28. A solid dental amalgam forming composition as in claim 12, wherein the solid amalgamable composition comprises a 40%–75% Ag alloy.

29. A solid composition in claim 12, wherein said solid compositions are in powder form.

30. A solid composition as in claim 29 wherein the average particle size of the powder is about 45 microns.

31. A solid composition as in claim 12, wherein said solid compositions are in pellitized form.

32. A solid dental amalgam forming composition as in claim 12 in unit dosage form.

33. A solid dental amalgam forming composition as in claim 32 wherein the unit dosage form is contained in a capsule.

34. A method for forming a dental amalgam by triturating together
(a) a solid amalgamating composition comprising one or more solid reincur containing alloys, or intermetallic compounds or combinations thereof, and
(b) a n amalgamable composition comprising one or more solid amaigamable alloys, metals and/or intermetallic compounds or combinations thereof.

35. The method of claim 34, wherein the solid amalgamating composition, comprises $Mn_2Hg_5$.

36. The method of claim 34, wherein the solid amalgamating composition, comprises an alloy of indium and mercury, which is a solid at room temperature.

37. The method of claim 34, wherein the solid amalgamating composition, comprises $Mn_2Hg_5$ and an alloy or alloys of indium and mercury, all of which are solid at room temperature.

38. The method of claim 34, wherein the solid amalgamating composition, additionally comprises free indium metal.

39. The method of claim 34, wherein the solid amalgamating composition, comprises $PdHg_4$ and an alloy or alloys of palladium and mercury, all of which are solid at room temperature.

40. The method of claim 39, wherein the solid amalgamating composition, further comprises $Ag_xHg_y$, wherein $1/3<x/y<2$.

41. The method of claim 39, wherein the solid amalgamating composition, further comprises tin metal or alloys of tin.

42. A method of claim 39, comprising an alloy of indium and mercury, which is a solid at room temperature.

43. The method of claim 41, wherein the tin alloy is a eutectic of tin with indium or silver.

44. A solid amalgamating composition as in claim 41, wherein tin alloy is a tin mercury allow solid at room temperature.

45. The method of claim 34, wherein the solid amalgamable composition is silver based.

46. The method of claim 34, wherein the solid amaigamable composition contains 45%–80% silver, 5%–30% copper, 10–35% tin and 0.1%–5% noble metal selected from the group consisting of gold, platinum, palladium or mixtures thereof, and may be further optionally alloyed with one or more of the following; 0.1%–10% indium, 0.1%–5% mercury, 0.1%–5% zinc or any mixtures thereof.

47. The method of claim 34, wherein the solid amalgamable composition contains copper, in an amount between 20%–40%.

48. The method of claim 34, wherein the solid amalgamable composition contains between 1%–8% of palladium, gold, platinum or any mixture thereof.

49. The method of claim 45, wherein the silver based component of the amalgamable composition is initially heat treated to increase amalgam working time.

50. The method of claim 34, wherein the solid amalgamable composition comprises a 40%–75% Ag alloy.

51. The method of claim 34, wherein said solid compositions are in powder form.

52. The dental amalgam of claim 51 wherein the average particle size of the powder is about 45 microns.

53. The method of claim 34, wherein said solid compositions are in pellitized.

54. The method of claim 34, implemented in unit dosage form.

55. The method of claim 54, wherein the unit dosage form is contained in a capsule.

56. Dental amalgam prepared by trituration together of
(a) a solid amalgamating composition comprising one or more solid mercury containing alloys, or intermetallic compounds or combinations thereof, and
(b) an amalgamable composition comprising one or more solid amalgamable alloys, metals and/or intermetallic compounds or combinations thereof.

57. The dental amalgam of claim 56, wherein the solid amalgamating composition, comprises $Mn_2Hg_5$.

58. The dental amalgam of claim 56, wherein the solid amalgamating composition, comprises an alloy of indium and mercury, which is a solid at room temperature.

59. The dental amalgam of claim 56, wherein the solid amalgamating composition, comprises $Mn_2Hg_5$ and an alloy or alloys of indium and mercury, all of which are solid at room temperature.

60. The dental amalgam of claim 56, wherein the solid amalgamating composition, additionally comprises free indium metal.

61. The dental amalgam of claim 56, wherein the solid amalgamating composition, comprises $PdHg_4$ and an alloy or alloys of palladium and mercury, all of which are solid at room temperature.

62. The dental amalgam of claim 61, wherein the solid amalgamating composition, further comprises $Ag_xHg_y$, wherein $1/3<x/y<2$.

63. The dental amalgam of claim 61, wherein the solid amalgamating composition, further comprises tin metal or alloys of tin.

64. The dental amalgam of claim 61, further comprising an alloy of indium and mercury, which is a solid at room temperature.

65. The dental amalgam of claim 63 wherein the tin tin alloy is a eutectic of tin with indium or silver.

66. The dental amalgam as in claim 63 wherein the tin alloy is a tin mercury alloy solid at room temperature.

67. The dental amalgam of claim 56, wherein the solid amalgamable composition is silver based.

68. The dental amalgam of claim 56, wherein the solid amalgamable composition contains 45%–80% silver, 5%–30% copper, 10–35% tin and 0.1%–5% noble metal selected from the group consisting of gold, platinum, palladium or mixtures thereof, and may be further optionally alloyed with one or more of the following; 0.1%–10% indium, 0.1%–5% mercury, 0.1%–5% zinc or any mixtures thereof.

69. The dental amalgam of claim 56, wherein the solid amalgamable composition contains copper in an amount between 20%–40%.

70. The dental amalgam of claim 56, wherein the solid amalgamable composition contains between 1%–8% of palladium, gold, platinum or any mixture thereof.

71. The dental amalgam of claim 67, wherein the silver based component of the amalgamable composition is initially heat treated to increase amalgam working time.

72. The dental amalgam of claim 56, wherein the solid amalgamable composition comprises a 40%–75% Ag alloy.

73. The dental amalgam of claim 56 wherein said solid compositions are in a powder form.

74. The dental amalgam of claim 73 wherein the average particle size of the powder is about 45 microns.

75. The dental amalgam of claim 56, wherein said solid compositions are in pellitized form.

76. The dental amalgam of claim 56, implemented in unit dosage form.

77. The dental amalgam of claim 76, wherein the unit dosage form is contained in a capsule.

78. A dental amalgam as in claim 56 whose composition is substantially as follows: manganese 0–5%, indium 0–15%, mercury 20–57%, silver 20–40%, copper 15–40%, palladium 0–8% and tin 3–5%.

* * * * *

UNITED STATES PATENT AND TRADEMARK OFFICE
CERTIFICATE OF CORRECTION

PATENT NO. : 6,190,606 B1
DATED : February 20, 2001
INVENTOR(S) : Kaufman

It is certified that error appears in the above-identified patent and that said Letters Patent is hereby corrected as shown below:

Claim 1,
Line 3 thereof, "With" should read, "with".

Claim 34,
In the second line of paragraph (a), "reincur" should read, "mercury".
In the first line of paragraph (b), "a n" should read "an".
In the second line of paragraph (b), "amaigamable" should read "amalgamable".

Claim 44,
Line 2 thereof, "allow" should read, "alloy".

Claim 53,
Line 2 thereof, "form" should follow "pelletized".

Signed and Sealed this

Ninth Day of October, 2001

Attest:

*Attesting Officer*

NICHOLAS P. GODICI
*Acting Director of the United States Patent and Trademark Office*